US005520991A

United States Patent [19]

Eustatiu

[11] Patent Number: 5,520,991

[45] Date of Patent: May 28, 1996

[54] COSMETIC PREPARATIONS FOR REVITALIZING THE SKIN

[76] Inventor: Lucien Eustatiu, Residence de Croisset, 1 avenue E de Croisset, 06130 Grasse, France

[21] Appl. No.: 211,807

[22] PCT Filed: Oct. 29, 1993

[86] PCT No.: PCT/FR93/01077

§ 371 Date: Apr. 18, 1994

§ 102(e) Date: Apr. 18, 1994

[87] PCT Pub. No.: WO94/10974

PCT Pub. Date: May 26, 1994

[30] Foreign Application Priority Data

Nov. 6, 1992 [FR] France .................................. 92 13643

[51] Int. Cl.$^6$ ......................... A61K 35/78; A61K 31/74; A61K 33/42

[52] U.S. Cl. .................................... 424/195.1; 424/78.03; 424/601; 424/630; 424/639; 424/641; 424/646; 424/655; 424/665; 424/684; 424/724; 514/458; 514/474; 514/557

[58] Field of Search ............................. 424/195.1, 78.03, 424/601, 630, 639, 641, 646, 655, 665, 684, 724; 514/458, 474, 557

[56] References Cited

U.S. PATENT DOCUMENTS

| | | | |
|---|---|---|---|
| 4,369,180 | 1/1983 | Mihalovits | 514/21 |
| 4,806,525 | 2/1989 | Morganti | 514/21 |

FOREIGN PATENT DOCUMENTS

| | | | |
|---|---|---|---|
| 0330583 | 8/1989 | European Pat. Off. | A61K 7/48 |
| 1526996 | 5/1968 | France . | |
| 2590169 | 5/1987 | France | A61K 7/48 |
| 2631824 | 12/1989 | France | A61K 7/48 |

*Primary Examiner*—John W. Rollins
*Attorney, Agent, or Firm*—Young & Thompson

[57] ABSTRACT

Cosmetic preparations revitalizing the skin which use products for external usage on the human body and a product for internal usage on the human body. The products for external usage are comprised by two creams and one solution, which stimulate the epidermal cells and the fibroblasts of the derma, while protecting the epidermis, and the product for internal usage is comprised by small gelatin capsule which carry to the fibroblasts of the derma amino acids and aligo-elements.

12 Claims, No Drawings

COSMETIC PREPARATIONS FOR REVITALIZING THE SKIN

FIELD OF THE INVENTION

The present invention relates to the field of cosmetics.

The present invention concerns different cosmetic preparations which revitalize the skin, each preparation being enriched in vitamins.

The different preparations are usable externally, by simple spreading on the skin, and by the oral route.

These two application routes act synergetically.

BACKGROUND OF THE INVENTION

Numerous documents relate to epidermal and dermal problems.

Thus, the document FR-A-2.585.568 relates to new cosmetic compositions, comprising a lipid derivative of corneous cells which can improve the ability of the corneous layer to retain moisture. They are useful in the treatment of dry skin. When the lipid is used in combination with tensio-active agents, the above effect is improved. The cosmetic compositions can be present in any type of preparation, such as creams, milks, beauty masks, lip rouge, foundation base, capillary tonics and the like.

This document discloses different types of preparations which can permit the treatment of dry skin.

The document FR-A-2.631.824 relates to cosmetic compositions which include in combination a component formed of a mixture of essential aromatic oils extracted from plants selected from: Lavender, Geranium, Rosemary, Eucalyptus, Sage, Thyme, Juniper, Basil, myroxylon, Lahafil and a composition including vitamins A and E, of ginseng and gammalinoleic acid.

This document discloses the use of vitamins A and E and the use of plant extracts.

All of these documents treat the problem of revitalization of the skin only by simple external application, promoting the retention of water by the cells.

SUMMARY OF THE INVENTION

The present invention has for its object cosmetic preparations revitalizing the skin, of the type using products used externally on the human body and a product used internally of said human body, characterized by the fact that the products for external use are comprised by two creams and one solution, which stimulate the epidermal cells and the fibroblasts of the derma and which protect the epidermis and in which the product for internal use is formed of small gelatin capsules which carry to the epidermal cells and to the fibroblasts, among others, amino acids and oligo-elements.

The invention also has for its object cosmetic preparations characterized by the fact that the total mass of the product for internal use comprises 33.4 to 34.4 parts per 100, hereinafter represented by the percentage symbol %, of amino acids, 23.7 to 24.7% of lecithin, 22.1 to 23.1% of lyophilized royal jelly, 4.8 to 5.4% vitamin C, substantially 0.1% of vitamin B6, substantially 0.02% of vitamin B12, and substantially 0.02% of oligo-elements.

The invention also has for its object cosmetic preparations characterized by the fact that the amino acids are in equivalent proportions of lysine, serine, histidine, threonine, valine and/or leucine.

Another object of the present invention is to provide cosmetic preparations characterized by the fact that the oligo-elements are in the form of selenium, zinc, magnesium, iron, manganese, copper, potassium, cobalt, phosphorous, silicon, chromium and/or vanadium.

Another object of the present invention is to provide cosmetic preparations characterized by the fact that the mass of each cream for external use comprises substantially 1% of essential oil of camomile romaine, substantially 1.5% of royal jelly, substantially 2% of wheat germ oil, substantially 0.25% of vitamin A, substantially 0.25% of vitamin E, substantially 0.25% of vitamin F, substantially 0.5% of biostimulants, and substantially 0.5% of allantoin.

Another object of the invention is to provide cosmetic preparations characterized by the fact that one of the two creams for external use comprises a hydrating factor of vegetable origin which is substantially 2.5% of the mass of said cream for external usage.

Another object of the present invention is to provide cosmetic preparations characterized by the fact that the creams for external use use as an excipient an emulsion of the oil-in-water type.

Another object of the invention is to provide cosmetic preparations characterized by the fact that the creams for external use have a pH substantially equal to 6.8.

Another object of the invention is to provide cosmetic preparations characterized by the fact that the mass of the solution for external use comprises 9.5 to 10.5% of extracts of Aloe Vera enriched in biostimulants, substantially 0.25% of vitamin A, substantially 0.25% of vitamin E, and substantially 0.25% of vitamin F.

An object of the invention is to provide cosmetic preparations characterized by the fact that the solution for external use uses as an excipient vegetable extracts enriched in natural hydrating factor.

Finally, the present invention has for its object the use of cosmetic preparations characterized by the fact that the application of the solution for external use precedes the application of the cream for external use which comprises the hydrating factor of vegetable origin.

DETAILED DESCRIPTION OF THE INVENTION

The description which follows is only by way of example and is not limiting, of the cosmetic preparations of the invention.

The present invention has the advantage of treating the skin as it is, which is to say a complex organ of our organism.

Thus, it is necessary to impart to it a stimulation from the exterior but above all to supply it from the interior with the combination of substances necessary for the biosynthesis of elastin and collagen, which will permit the skin to respond favorably to the external stimulation.

The external stimulation is by external factors such as biostimulants which have a role of general stimulation for all the epidermal cells as well as the fibroblasts of the derma which synthesize the elastic matrix formed of collagen and elastin.

This biosynthesis of the fibroblasts depends on the content of the specific amino acids which are lacking in the organism.

These substances, as well as the vitamins and oligo-elements indispensable to this synthesis, can be supplied by the blood, from which arises the need to use an internal factor in the form of a dietetic product specific to the skin.

From this fact, the cosmetic preparations regenerating the skin are of the type using products for external use on the human body but also a product for internal use in said human body.

The products for external use stimulate all of the epidermal cells as well as the fibroblasts located in the derma and, moreover, permit the revitalization and hydration of the epidermis.

The product for internal use, for its part, carries several elements such as the amino acids and the oligo-elements.

Nevertheless, it is well to specify that a mixture comprising a random mixture of vitamins, oligo-elements and amino acids is not necessarily the most effective.

The product for internal use is comprised by amino acids, lecithin, lyophilized royal jelly, vitamins and oligo-elements.

The products for external use are comprised by two creams and one solution.

The creams for external use are comprised of essential oils, camomile romaine, lyophilized royal jelly and wheat germ oil, vitamins, biostimulants and allantoin, while the solution for external use is comprised by vitamins, extracts of Aloe Vera, and biostimulants.

The solution for external use uses as an excipient vegetable extracts enriched in natural hydrating factor such as tea extracts.

As to the product for internal use, the mass of this latter comprises 33.9% of amino acids.

These amino acids are, in equivalent proportion to each other, lysine, serine, histidine, threonine, valine and/or leucine.

The mass of the product for internal use comprises also 24.2% of lecithin, 22.6% of lyophilized royal jelly, 19.7% of vitamins of which the vitamins C, B6 and B12 that are present in the respective following proportions: 5.1%, 0.1% and 0.02%.

The oligo-elements are numerous and essential in the biosynthesis of elastin and collagen.

They comprise selenium, zinc, magnesium, iron, manganese, copper, potassium, cobalt, germanium, phosphorus, silicon, chromium and/or vanadium.

The oligo-elements are in substantially equivalent proportion to each other and comprise 0.02% of the mass of the product for internal use.

The two creams for external usage have a composition that is identical apart from one element.

Thus, the mass of each cream for external use comprises 1% essential oil of camomile romaine, 1.5% of royal jelly, 2% of wheat germ oil, 0.75% of vitamins distributed in equal proportion between vitamins A, E and F, 0.5% of biostimulants and 0.5% of allantoin.

One of the two creams, for day-time use, comprises moreover a hydrating factor of vegetable origin which is present in a proportion of 2.5% in the mass of the cream for external use that contains it.

The other cream is for night-time use.

The creams for external use, whether day time or night time, use as excipient an emulsion of the oil-in-water type which permits having creams for external use which have the property of having a high pH equal to 6.8.

The last product of these cosmetic preparations is the solution for external usage.

The mass of this latter comprises 10% of Aloe Vera extracts, 0.5% biostimulants, but also 0.75% of vitamins distributed in the following fashion: 0.25% of vitamins A, 0.25% of vitamin E and 0.25% of vitamin F.

This solution for external use has for its excipient vegetable extracts enriched in natural hydrating factor, such as tea extracts.

Numerous studies and tests under dermatological hospital conditions have permitted establishing the safety of the cosmetic preparations of the present invention and demonstrating the revitalizing regenerating action of these latter.

The object of these studies has been to ascertain the properties of complete treatment utilizing the two creams, one for day, the other for night, and the solution, as well as the product for internal usage, this latter being present in the form of small gelatin capsules.

A study of the results has been possible because the two creams have been applied over all the face while the solution has been applied only on the right-hand half of the face.

This has been performed on six volunteer adult subjects for a total of 40 days.

The results which are given below represent the measures taken from the first through the fortieth day.

The administration of the small gelatin capsules was daily, three times per day which is to say morning, noon and night.

The application of the day regenerating cream was daily, at 8:00 o'clock in the morning.

The use of the regenerating and firming night cream was daily, at about 10:00 p.m.

The use of the solution was daily, about 8:00 a.m.

The use of the solution always precedes the application of the regenerating and hydrating day cream.

Prints on the skin were produced with the help of a synthetic polymer especially used for this purpose.

The reading of the prints permitted identifying two zones: the flat portions and the wrinkles on the forehead.

The results are expressed in percentages corresponding to the surface of the skin forming the flat regions and the wrinkles relative to 100% of the skin surface studied as a reference.

TABLE I

| | STUDIES OF FLAT SURFACES | |
|---|---|---|
| | Right Side (%) | Left Side (%) |
| DAY 1 | 65.05 | 65.98 |
| DAY 40 | 67.81 | 66.47 |

There will be noted from this table, the tendency to enlarge the flat areas.

However, between the right side and the left side an important difference appears.

Between day 1 designated DAY 1 and day 40 designated DAY 40, there will be noted on the right side an increase of 2.76% of the surface of the flat areas, while on the left side the increase is only 0.49%.

It therefore appears clearly that the right side half face to which was applied the solution, has developed more favorably than the left side half face.

TABLE II

| STUDY OF WRINKLES | | |
|---|---|---|
| | Right Side (%) | Left Side (%) |
| DAY 1 | 31.54 | 30.31 |
| DAY 40 | 28.58 | 30.07 |

Here again, the effects on the depths of the wrinkles are not the same between the right side and the left side.

The differences which exist between the two sides are even more important.

It will be noted that respectively the right side has a decrease of 2.96% of the surplus area of the wrinkles, while on the left side this decrease is only 0.24%.

Here again, the presence of the solution containing biostimulants permits acting directly on the epidermal cells.

TABLE III

| STUDY OF THE THICKNESS OF THE EPIDERMIS | | |
|---|---|---|
| | DAY 1 (micrometers) | DAY 40 (micrometers) |
| 1st subject | 56.88 | 67.18 |
| 2nd subject | 60.94 | 76.29 |
| 3rd subject | 60.63 | 61.15 |
| 4th subject | 56.20 | 62.41 |
| 5th subject | 64.99 | 68.78 |
| 6th subject | 61.98 | 70.68 |

From this last table will be better understood the variations of the right-half side of the face of the subjects.

Thus, between the first and fortieth day of treatment, the six subjects, whose thickness of epidermis are indicated in the above table, show a substantial thickening of said epidermis.

This method consists therefore in treating the skin from the exterior and the interior at the same time with complementary active substances which act at the tissue level of the skin, while taking part together in the processes of revitalization of said skin with proven effects on the thickening of the skin, on its hydration, on the enlargement of the flat surfaces and on the diminution of the wrinkles.

The effects on the derma are the increase of the elastin and collagen fibers which add themselves to the pre-existing fibers, which redounds to the advantage of the skin.

I claim:

1. Cosmetic preparation for regenerating the skin, comprising: products for external usage on the human body and a product for internal usage on said human body, said products for external usage comprising a) two creams comprised of essential oils, wheat germ oil, vitamins, biostimulants and allantoin, and b) one solution comprised of Aloe Vera extracts, biostimulants and vitamins, said two creams and one solution working together to stimulate the epidermal cells and the fibroblasts of the derma, and to protect the epidermis, and said product for internal usage comprised of amino acids, lecithin, lyophilized royal jelly, vitamins and oligo-elements.

2. Preparation according to claim 1, wherein the total mass of the product for internal usage comprises:

from 33.4 to 34.4% of amino acids, from 23.7 to 24.7% of lecithin, from 22.1 to 23.1% of lyophilized royal jelly, from 4.8 to 5.4% of vitamin C, substantially 0.1% of vitamin B6, substantially 0.02% of vitamin B12, and substantially 0.02% of oligo-elements.

3. Preparation according to claim 1, wherein the amino acids are selected from the group consisting of lysine, serine, histidine, threonine, valine and leucine, said amino acids being present in equivalent proportions.

4. Preparation according to claim 1, wherein the oligo-elements are selected from the group consisting of selenium, zinc, magnesium, iron, manganese, copper, potassium, cobalt, germanium, phosphate, silicon, chrome and vanadium.

5. Preparation according to claim 1, wherein the mass of each cream for external usage comprises:

substantially 1% of essential oil of camomile romaine, substantially 1.5% of royal jelly, substantially 2% of wheat germ oil, substantially 0.25% of vitamin A, substantially 0.25% of vitamin E, substantially 0.25% of vitamin F, substantially 0.5% of biostimulants, and substantially 0.5% of allantoin.

6. Preparation according to claim 1, wherein one of the two creams is for day-time use and additionally comprises a hydrating factor of vegetable origin representing substantially 2.5% of the mass of said cream for day-time use.

7. Preparation according to claim 1, wherein the creams for external usage use as an excipient an emulsion of the oil-in-water type.

8. Preparation according to claim 1, wherein the creams for external usage have a pH of about 6.8.

9. Preparation according to claim 1, wherein the mass of the solution for external usage comprises:

from 9.5 to 10.5% of extracts of Aloe Vera, substantially 0.5% of biostimulants, substantially 0.25% of vitamin A, substantially 0.25% of vitamin E, and substantially 0.25% of vitamin F.

10. Preparation according to claim 1, wherein the solution for external usage utilizes as an excipient vegetable extracts enriched in natural hydrating factor.

11. Preparation according to claim 1, wherein use of the solution for external usage precedes the application of one of the creams for external usage.

12. Preparation according to claim 1, wherein the product for internal usage is in the form of gelatin capsules, which carry said amino acids and oligo-elements to the epidermal cells and to the fibroblasts.

* * * * *